(12) United States Patent
Srinivasan et al.

(10) Patent No.: US 11,261,160 B2
(45) Date of Patent: Mar. 1, 2022

(54) PROCESS FOR THE PREPARATION OF N-(4-(6,7-DIMETHOXYQUINOLIN-4-YLOXY)PHENYL)-N'-(4-FLUOROPHENYL) CYCLOPROPANE-1, 1-DICARBOXAMIDE, (2S)-HYDROXYBUTANEDIOATE AND ITS POLYMORPHS THEREOF

(71) Applicants: MSN LABORATORIES PRIVATE LIMITED, R&D CENTER, Telangana (IN); Thirumalai Rajan Srinivasan, Hyderabad (IN); Eswaraiah Sajja, Hyderabad (IN); Venkata Panakala Rao Gogulapati, Hyderabad (IN); Rajeshwar Reddy Sagyam, Hyderabad (IN); Shyam Kiran Babu Gandham, Hyderabad (IN); Rajesham Boge, Hyderabad (IN)

(72) Inventors: Thirumalai Rajan Srinivasan, Hyderabad (IN); Eswaraiah Sajja, Hyderabad (IN); Venkata Panakala Rao Gogulapati, Hyderabad (IN); Rajeshwar Reddy Sagyam, Hyderabad (IN); Shyam Kiran Babu Gandham, Hyderabad (IN); Rajesham Boge, Hyderabad (IN)

(73) Assignee: MSN LABORATORIES PRIVATE LIMITED, R&D CENTER, Telangana (IN)

( * ) Notice: Subject to any disclaimer, the term of this patent is extended or adjusted under 35 U.S.C. 154(b) by 465 days.

(21) Appl. No.: 16/467,853

(22) PCT Filed: Dec. 6, 2017

(86) PCT No.: PCT/IN2017/000139
§ 371 (c)(1),
(2) Date: Jun. 7, 2019

(87) PCT Pub. No.: WO2018/104954
PCT Pub. Date: Jun. 14, 2018

(65) Prior Publication Data
US 2021/0403431 A1    Dec. 30, 2021

(30) Foreign Application Priority Data

Dec. 7, 2016  (IN) ............................. 201641041767
Jun. 15, 2017 (IN) ............................. 201741020998

(51) Int. Cl.
*C07D 215/233* (2006.01)

(52) U.S. Cl.
CPC ...... *C07D 215/233* (2013.01); *C07B 2200/13* (2013.01)

(58) Field of Classification Search
CPC ..................... C07D 215/233; C07B 2200/13
See application file for complete search history.

(56) References Cited

U.S. PATENT DOCUMENTS

2017/0096395 A1* 4/2017 Jetti .................. C07D 215/233

FOREIGN PATENT DOCUMENTS

WO       WO2015177758       11/2015

OTHER PUBLICATIONS (ISA/210) International Search Report mailed by the Patent Cooperation Treaty (PCT) dated Mar. 12, 2018.
(ISA/237) Written Opinion of the International Searching Authority mailed by the Patent Cooperation Treaty (PCT) dated Mar. 12, 2018.

* cited by examiner

*Primary Examiner* — Timothy R Rozof
(74) *Attorney, Agent, or Firm* — IP Pundit LLC (57) ABSTRACT

The present invention also relates to process for the preparation of N-(4-(6,7-dimethoxy quinolin-4-yloxy)phenyl)-N'-(4-fluorophenyl)cyclopropane-1,1-dicarboxamide (S)-malate compound of formula-1a and its polymorphs thereof, represented by the following structural:

Formula-1

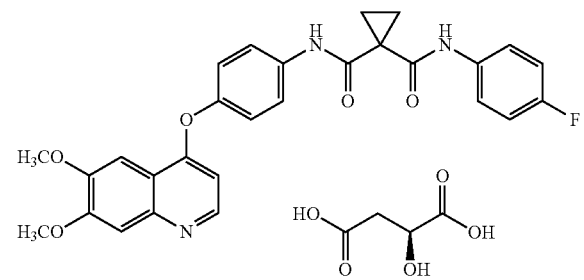

15 Claims, 3 Drawing Sheets

PROCESS FOR THE PREPARATION OF N-(4-(6,7-DIMETHOXYQUINOLIN-4-YLOXY)PHENYL)-N'-(4-FLUOROPHENYL) CYCLOPROPANE-1, 1-DICARBOXAMIDE, (2S)-HYDROXYBUTANEDIOATE AND ITS POLYMORPHS THEREOF

RELATED APPLICATIONS

This application claims the benefit of priority of our Indian patent application numbers 201641041767 filed on 7 Dec. 2016 and 201741020998 filed on 15 Jun. 2017 which are incorporated herein by reference.

FIELD OF THE INVENTION

The present invention relates to novel crystalline forms of N-(4-(6,7-dimethoxy quinolin-4-yloxy)phenyl)-N'-(4-fluorophenyl)cyclopropane-1,1-dicarboxamide (S)-malate compound of formula-1a.

Formula-Ia

The present invention also relates to novel crystalline forms of N-(4-(6,7-dimethoxy quinolin-4-yloxy)phenyl)-N'-(4-fluorophenyl)cyclopropane-1,1-dicarboxamide hydrochloride salt compound of formula-1b.

BACKGROUND OF THE INVENTION

Cabozantinib (S)-malate is a kinase inhibitor indicated for the treatment of patients with progressive, metastatic medullary thyroid cancer and advanced renal cell carcinoma in people who have received prior anti-angiogenic therapy.

Cabozantinib has been approved by the US FDA as COMETRIQ for the treatment of patients with progressive, metastatic medullary thyroid cancer.

COMETRIQ has also been approved by the European Commission for the Treatment of adult patients with progressive, unresectable locally advanced or metastatic medullary thyroid carcinoma.

Cabozantinib chemically known as N-{4-[(6,7-dimethoxyquinolin-4-yloxy]phenyl}-M-(4-fluorophenyl) cyclopropane-1,1-dicarboxamide.

International (PCT) publication No. WO 2005030140 A1 first disclosed Cabozantinib and process for its preparation.

International (PCT) publication No. WO 2010083414 A1 discloses amorphous forms of Cabozantinib L- and D-malate as well as the N-1 and N-2 polymorphs of crystalline Cabozantinib L- and D-malate and process for its preparation.

International (PCT) publication No. WO 2016150966 A1 discloses crystalline Cabozantinib hydrochloride as well as crystalline Cabozantinib phosphate and process for its preparation.

CN104961680 A discloses crystal A and crystal 13 of hydrochloride salt of Cabozantinib and process for its preparation.

CN194961681 A discloses various acid addition salts of Cabozantinib and process for its preparation.

BRIEF DESCRIPTION OF THE INVENTION

The first aspect of the present invention is to provide novel crystalline form of N-(4-(6,7-dimethoxyquinolin-4-yloxy)phenyl)-N'-(4-fluorophenyl)cyclopropane-1,1-dicarboxamide hydrochloride salt compound of formula-1b, herein after designated as form-M and process for its preparation.

The second aspect of the present invention is to provide an improved process for the preparation of N-(4-(6,7-dimethoxyquinolin-4-yloxy)phenyl)-N'-(4-fluorophenyl)cyclo propane-1,1-dicarboxamide (S)-malate compound of formula-1a.

The third aspect of the present invention is to provide novel crystalline form of N-(4-(6,7-dimethoxyquinolin-4-yloxy)phenyl)-N'-(4-fluorophenyl)cyclopropane-1,1-dicarboxamide hydrochloride salt compound of formula-1b, herein after designated as form-S and process for its preparation.

The fourth aspect of the present invention is to provide novel crystalline form of N-(4-(6,7-dimethoxyquinolin-4-yloxy)phenyl)-N'-(4-fluorophenyl)cyclopropane-1,1-dicarboxamide hydrochloride salt compound of formula-1b, herein after designated as form-N and process for its preparation.

The fifth aspect of the present invention is to provide novel crystalline form of N-(4-(6,7-dimethoxyquinolin-4-yloxy)phenyl)-N'-(4-fluorophenyl)cyclopropane-1,1-dicarboxamide hydrochloride salt compound of formula-1b, herein after designated as form-R and process for its preparation.

The sixth aspect of the present invention is to provide novel crystalline form of N-(4-(6,7-dimethoxyquinolin-4-yloxy)phenyl)-N'-(4-fluorophenyl)cyclopropane-1,1-dicarboxamide (S)-malate compound of formula-1a, herein after designated as form-M and process for its preparation.

The seventh aspect of the present invention is to provide novel crystalline form of N-(4-(6,7-dimethoxyquinolin-4-yloxy)phenyl)-N'-(4-fluorophenyl)cyclopropane-1,1-dicarboxamide (S)-malate compound of formula-1a, herein after designated as form-S and process for its preparation.

The eighth aspect of the present invention is to provide a process for the preparation of crystalline form-S of N-(4-(6,7-dimethoxyquinolin-4-yloxy)phenyl)-N'-(4-fluorophenyl) cyclopropane-1,1-dicarboxamide (S)-malate compound of formula-1a.

BRIEF DESCRIPTION OF THE DRAWINGS

FIG. 5: Illustrates the PXRD pattern of crystalline form-M of N-(4-(6,7-dimethoxy quinolin-4-yloxy)phenyl)-N'-(4-fluorophenyl)cyclopropane-1,1-dicarboxamide (S)-malate compound of formula-1a.

FIG. 6: Illustrates the PXRD pattern of crystalline form-S of N-(4-(6,7-dimethoxyquinolin-4-yloxy)phenyl)-N'-(4-fluorophenyl)cyclopropane-1,1-dicarboxamide (S)-malate compound of formula-1a.

DETAILED DESCRIPTION OF THE INVENTION

As used herein the term "suitable solvent" used in the present invention refers to "hydrocarbon solvents" such as n-hexane, n-heptane, cyclohexane, pet ether, toluene, pentane, cycloheptane, methylcyclohexane, m-, o-, or p-xylene, and the like; "ether solvents" such as dimethoxy methane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, 1,2-dimethoxy ethane and the like; "ester solvents" such as methyl acetate, ethyl acetate, isopropyl acetate, n-butyl acetate and the like; "polar-aprotic solvents such as dimethylacetamide (DMA), dimethylformamide (DMF), dimethyl sulfoxide (DMSO), N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutylketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol, 2-nitroethanol, 2-fluoroethanol, 2,2,2-trifluoroethanol, ethylene glycol, propylene glycol, 2-methoxyethanol, 1,2-ethoxyethanol, diethylene glycol, 1, 2, or 3-pentanol, neo-pentyl alcohol, t-pentyl alcohol, diethylene glycol monoethyl ether, cyclohexanol, anisole, benzyl alcohol, phenol, or glycerol and the like; "polar solvents" such as water or mixtures thereof.

The term "suitable base" used herein the present invention until unless specified is selected from inorganic bases like "alkali metal hydroxides" such as lithium hydroxide, sodium hydroxide, potassium hydroxide and the like; "alkali metal carbonates" such as Sodium carbonate, potassium carbonate, lithium carbonate and the like; "alkali metal bicarbonates" such as sodium bicarbonate, potassium bicarbonate, lithium bicarbonate and the like; "alkali metal hydrides" such as potassium hydride, lithium hydride and the like; ammonia; and organic bases such "alkali metal alkoxides" such as sodium methoxide, sodium ethoxide, sodium tert-butoxide, potassium methoxide, potassium ethoxide, potassium tert-butoxide and the like; triethyl amine, methyl amine, ethyl amine, 1,8-diazabicyclo [5.4.0]undec-7-ene (DBU), 1,5-diazabicyclo(4.3.0)non-5-ene (DBN), lithium dioisopropyl amide (LDA), n-butyl lithium, tribenzylamine, isopropyl amine, diisopropyl amine, diiso propylethylamine, N-methylmorpholine, N-ethylmorpholine, piperidine, dimethylamino pyridine, morpholine, pyridine, 2,6-lutidine, 2,4,6-collidine, imidazole, 1-methyl imidazole, 1,2,4-triazole, 1,4-diazabicyclo[2.2.2]octane (DABCO) or mixtures thereof.

The "hydrochloric acid source" used herein the present invention is selected from hydrochloric acid gas, aqueous hydrochloric acid, ethanolic-HCl, methanolic-HCl, ethyl acetate-hydrochloric acid, isopropanol-hydrochloric acid, diisopropyl, ether-hydrochloric acid, diethylether-hydrochloric acid, and trimethylchlorosilane.

Figure 1:
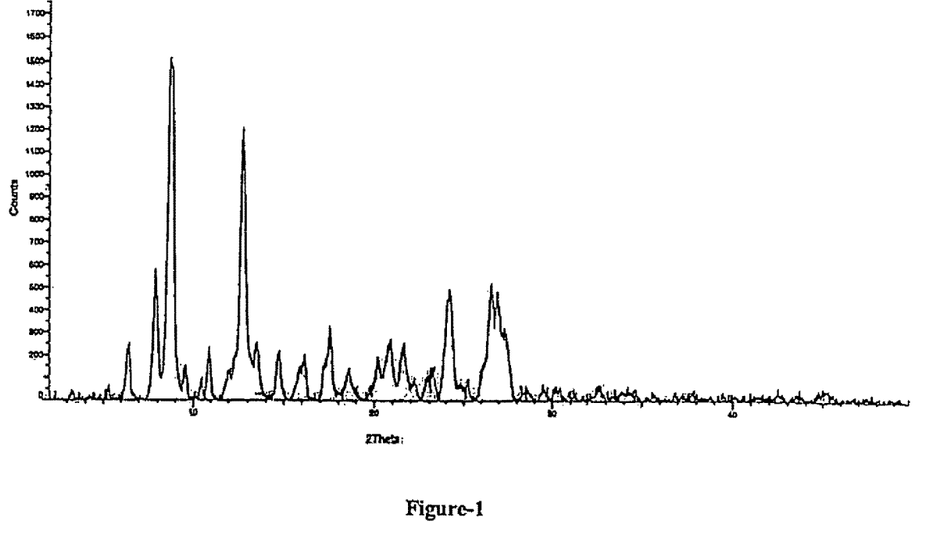
FIG. 1: Illustrates the PXRD pattern of crystalline form-M of N-(4-(6,7-dimethoxy quinolin-4-yloxy)phenyl)-N'-(4-fluorophenyl)cyclopropane-1,1-dicarboxamide hydrochloride salt compound of formula-1b.

The first aspect of the present invention provides a crystalline form-M of N-(4-(6,7-dimethoxyquinolin-4-yloxy)phenyl)-N'-(4-fluorophenyl)cyclopropane-1,1-dicarboxamide hydrochloride salt compound of formula-1b, characterized by its powder x-ray diffraction pattern having peaks at 6.4, 7.8, 8.6, 9.5, 10.4, 10.8, 12.0, 12.7, 13.4, 14.7, 16.0, 17.2, 17.5, 18.6, 20.2, 20.8, 21.5, 22.1, 22.7, 23.2, 24.1, 26.5, 26.8 and 27.2±0.2 degrees two theta as depicted in figure-1.

Further, In an embodiment of the present invention also provides a process for the preparation of crystalline form-M of N-(4-(6,7-dimethoxyquinolin-4-yloxy)phenyl)-N'-(4-fluorophenyl)cyclopropane-1,1-dicarboxamide hydrochloride salt compound of formula-1b, comprising of:
a) Adding a suitable solvent to N-(4-(6,7-dimethoxyquinolin-4-yloxy)phenyl)-N'-(4-fluorophenyl)cyclopropane-1,1-dicarboxamide hydrochloride salt of compound of formula-1b.
b) stirring the reaction mixture for 3 hours at 25-30° C.,
c) filtering the reaction mixture and drying to get crystalline form-M of N-(4-(6,7-dimethoxyquinolin-4-yloxy)phenyl)-N'-(4-fluorophenyl)cyclopropane-1,1-dicarboxamide hydrochloride salt compound of formula-1b.

Wherein, in step-a) the suitable solvent is selected from chloro solvents, alcohol solvents, ester solvents, nitrile solvents, polar aprotic solvents, hydrocarbon solvents, ether solvents, ketone solvents, polar solvents such as water or mixtures.

The preferred embodiment of the present invention provides a process for the preparation of crystalline form-M of N-(4-(6,7-dimethoxyquinolin-4-yloxy)phenyl)-N'-(4-fluorophenyl)cyclopropane-1,1-dicarboxamide hydrochloride salt compound of formula-1b, comprising of:
a) Adding isopropanol to N-(4-(6,7-dimethoxyquinolin-4-yloxy)phenyl)-W-(4-fluorophenyl)cyclopropane-1,1-dicarboxamide hydrochloride salt of compound of formula-1b,
b) stirring the reaction mixture for 3 hours at 25-30° C.,
c) filtering the reaction mixture and drying to get crystalline form-M of N-(4-(6,7-dimethoxyquinolin-4-yloxy)phenyl)-M-(4-fluorophenyl)cyclopropane-1,1-dicarboxamide hydrochloride salt compound of formula-1b.

The second aspect of the present invention provides an improved process for the preparation of N-(4-(6,7-dimethoxyquinolin-4-yloxy)phenyl)-N'-(4-fluorophenyl)cyclo propane-1,1-dicarboxamide (S)-malate compound of formula-1a, comprising of the following steps:
a) Reacting 1-((4-fluorophenyl)carbamoyl)cyclopropane carboxylic acid compound of formula-2 with chlorinating agent in a suitable solvent to provide 1-(4-fluorophenyl carbamoyl)cyclopropanecarbonylchloride compound of formula-3,
b) reacting the compound of formula-3 in-situ with 4-(6,7-dimethoxyquinolin-4-yloxy) aniline compound of formula-4 in the presence of a suitable base in a suitable solvent to provide N-(4-(6,7-dimethoxyquinolin-4-yloxy)phenyl)-N'-(4-fluorophenyl) cyclopropane-1,1-dicarboxamide compound of formula-1, c) treating the compound of formula-1 in-situ with a suitable hydrochloric acid source in a suitable solvent to provide N-(4-(6,7-dimethoxyquinolin-4-yloxy)phenyl)-N'-(4-fluorophenyl)cyclopropane-1,1-dicarboxamide hydrochloride salt compound of formula-1b, d) purifying the compound of formula-1b using a suitable solvent, e) treating the compound of formula-1b with a suitable base in a suitable solvent to provide N-(4-(6,7-dimethoxyquinolin-4-yloxy)phenyl)-N'-(4-fluorophenyl)cyclo propane-1,1-dicarboxamide compound of formula-1 which on in-situ treating with (L)-malic acid in a suitable solvent to provide N-(4-(6,7-dimethoxyquinolin-4-yloxy) phenyl)-N'(4-fluorophenyl)cyclopropane-1,1-dicarboxamide (S)-malate compound of formula-1a.

Wherein, in step-a) the suitable chlorinating agent is selected from pivaloyl chloride, thionyl chloride, sulfuryl chloride, phosphorus oxychloride, oxalyl chloride, phosphorus trichloride, phosphorus pentachloride; in step-b) & step-e) the suitable base is selected from inorganic or organic base; in step-c) the suitable hydrochloric acid source is selected from hydrochloric acid gas, aqueous hydrochloric acid, ethyl acetate-hydrochloric acid, ethanolic-HCl, methanolic-HCl, isopropanol-hydrochloric acid, diisopropyl ether-hydrochloric acid, diethylether-hydrochloric acid, and trimethylchlorosilane;

in step-a) to step-e) the suitable solvent is selected from chloro solvents, alcohol solvents, ester solvents, nitrile solvents, polar aprotic solvents, hydrocarbon solvents, ether solvents, ketone solvents, polar solvents such as water or mixtures.

The preferred embodiment of the present invention provides an improved process for the preparation of N-(4-(6,7-dimethoxyquinolin-4-yloxy)phenyl)-N'-(4-fluorophenyl)cyclo propane-1,1-dicarboxamide (S)-malate compound of formula-1a, comprising of the following steps:

a) Reacting 1-((4-fluorophenyl)carbamoyl)cyclopropane carboxylic acid compound of formula-2 with thionyl chloride in tetrahydrofuran to provide 1-(4-fluorophenyl carbamoyl)cyclopropanecarbonylchloride compound of formula-3, b) reacting the compound of formula-3 in-situ with 4-(6,7-dimethoxyquinolin-4-yloxy) aniline compound of formula-4 in the presence of potassium carbonate in a mixture of water and tetrahydrofuran to provide N-(4-(6,7-dimethoxyquinolin-4-yloxy)phenyl)-N'-(4-fluorophenyl)cyclopropane-1,1-dicarboxamide compound of formula-1, c) treating the compound of formula-1 in-situ with aqueous hydrochloric acid to provide N-(4-(6,7-dimethoxyquinolin-4-yloxy)phenyl)-N'-(4-fluorophenyl)cyclopropane-1,1-dicarboxamide hydrochloride salt compound of formula-1b, d) purifying the compound of formula-1b using isopropanol and then followed by using dimethyl sulfoxide and ethyl acetate, e) treating the compound of formula-1b with aqueous sodium carbonate solution to provide N-(4-(6,7-dimethoxyquinolin-4-yloxy)phenyl)-N'-(4-fluorophenyl)cyclo propane-1,1-dicarboxamide compound of formula-1 which on in-situ treating with (L)-malic acid in a mixture of tetrahydrofuran, water and methyl isobutyl ketone to provide N-(4-(6,7-dimethoxyquinolin-4-yloxy)phenyl)-N'-(4-fluorophenyl)cyclo propane-1,1-dicarboxamide (S)-malate compound of formula-1a.

U.S. Pat. No. 7,579,473 B2 involves purification of crude Cabozantinib by preparative column chromatography which is expensive, tedious, time consuming and inevitably decrease yield of the product. Hence this process is not suitable for commercial scale. Therefore, there is an unmet need to develop a purification process which, can be performed at industrial scale.

The present invention have overcame the problems associated with the prior art, by simply converting the crude Cabozantinib into its acid addition salt and then treating the acid addition salt of Cabozantinib with a suitable base to provide Cabozantinib free base compound of formula-1 with enhanced purity.

N-(4-(6,7-dimethoxyquinolin-4-yloxy)phenyl)-N'-(4-fluorophenyl)cyclopropane-1,1-dicarboxamide (S)-malate compound of formula-1a obtained according to the present invention is having 1-((4-((6,7-dimethoxyquinolin-4-yloxy)phenyl)carbamoyl)cyclopropane carboxylic acid {M-Acid Impurity}; 1-((4-fluorophenyl)carbamoyl)cyclopropane carboxylic acid {Acid Impurity}; N-(4-fluorophenyl)-N-(4-hydroxyphenyl)cyclopropane-1,1-di carboxamide {Hydroxy Impurity}; N-(4-((6,7-dimethoxyquinolin-4-yloxy)phenyl)-N-phenyl cyclopropane-1,1-dicarboxamide {Desfluoro Impurity}; N-(4-((6,7-dimethoxyquinolin-4-yloxy)phenyl)-N-(2-fluorophenyl)cyclopropane-1,1-dicarboxamide {2-Fluoro Impurity}; 4-(4-(1-((4-fluorophenyl)carbamoyl)cyclopropanecarboxamido)phenoxy)-6,7-dimethoxyquinoline 1-oxide {N-Oxide Impurity}; N-(4-((6,7-dimethoxyquinolin-4-yloxy)phenyl)-N-(3-fluoro phenyl) cyclopropane-1,1-dicarboxamide {3-Fluoro Impurity}; and N-(4-((6,7-dimethoxy quinolin-4-yloxy)phenyl)-6,7-dimethoxyquinolin-4-amine {Dialer Impurity} less than 0.05% as measured by HPLC.

M-Acid Impurity

Desfluoro Impurity

Acid Impurity

Hydroxy Impurity

2-Fluoro Impurity

N-Oxide Impurity

-continued

3-Fluoro Impurity

Dimer Impurity

N-(4-(6,7-dimethoxyquinolin-4-yloxy)phenyl)-N'-(4-fluorophenyl)cyclopropane-1,1-dicarboxamide (S)-malate compound of formula-1a obtained according to the present invention is having particle size distribution $D_{90}<100$ μm.

Figure 2:
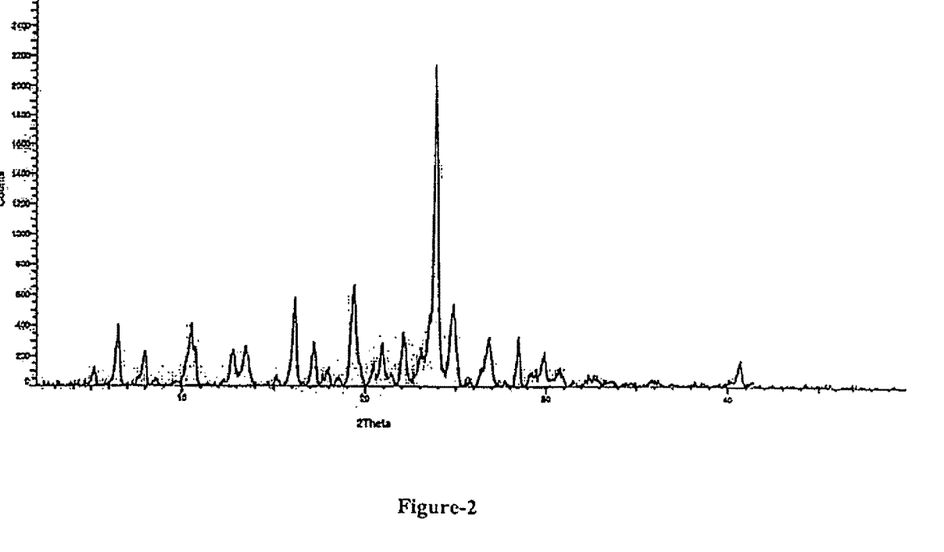
FIG. 2: Illustrates the PXRD pattern of crystalline form-S of N-(4-(6,7-dimethoxy quinolin-4-yloxy)phenyl)-N'-(4-fluorophenyl)cyclopropane-1,1-dicarboxamide hydrochloride salt compound of formula-1b.

The third aspect of the present invention provides a crystalline form-S of N-(4-(6,7-dimethoxyquinolin-4-yloxy)phenyl)-N'-(4-fluorophenyl)cyclopropane-1,1-dicarboxamide hydrochloric acid salt compound of formula-1b, characterized by its powder x-ray diffraction pattern having peaks at 5.1, 6.5, 7.9, 8.6, 9.7, 10.5, 12.8, 13.4, 15.2, 16.1, 17.2, 17.9, 18.5, 19.1, 19.4, 20.4, 20.9, 22.0, 23.0, 23.7, 24.8, 26.8, 28.4, 29.1, 29.8 and 40.6±0.2 degrees two theta as depicted in figure-2.

In another embodiment of the present invention provides a process for the preparation of crystalline form-S of N-(4-(6,7-dimethoxyquinolin-4-yloxy)phenyl)-N'-(4-fluorophenyl) cyclopropane-1,1-dicarboxamide hydrochloride salt compound of formula-1b, comprising of the following steps:
  a) Adding a suitable solvent to N-(4-(6,7-dimethoxyquinolin-4-yloxy)phenyl)-N'-(4-fluorophenyl)cyclopropane-1,1-dicarboxamide hydrochloride compound of formula-1b,
  b) stirring the reaction mixture,
  c) filtering the reaction mixture,
  d) adding a suitable solvent to the filtrate obtained in step-c),
  e) stirring the reaction mixture,
  f) filtering the precipitated solid and drying to get the crystalline form-S of N-(4-(6,7-dimethoxyquinolin-4-yloxy)phenyl)-N'-(4-fluorophenyl)cyclopropane-1,1-dicarboxamide hydrochloride salt compound of formula-1b.

Wherein, in step-a) and step-d) the suitable solvent is selected from chloro solvents, alcohol solvents, ester solvents, nitrile solvents, polar aprotic solvents, hydrocarbon solvents, ether solvents, ketone solvents, polar solvents such as water or mixtures.

The preferred embodiment of the present invention provides a process for the preparation of crystalline form-S of N-(4-(6,7-dimethoxyquinolin-4-yloxy)phenyl)-N'-(4-fluorophenyl)cyclopropane-1,1-dicarboxamide hydrochloride salt compound of formula-1b, comprising of the following steps:
  a) Adding dimethyl sulfoxide to N-(4-(6,7-dimethoxyquinolin-4-yloxy)phenyl)-N'-(4-fluorophenyl)cyclopropane-1,1-dicarboxamide hydrochloride compound of formula-1b,
  b) stirring the reaction mixture,
  c) filtering the reaction mixture,
  d) adding ethyl acetate to the filtrate obtained in step-c),
  e) stirring the reaction mixture,
  f) filtering the precipitated solid and drying to get the crystalline form-S of N-(4-(6,7-dimethoxyquinolin-4-yloxy)phenyl)-N'-(4-fluorophenyl)cyclopropane-1,1-dicarboxamide hydrochloride salt compound of formula-1b.

Figure 3:
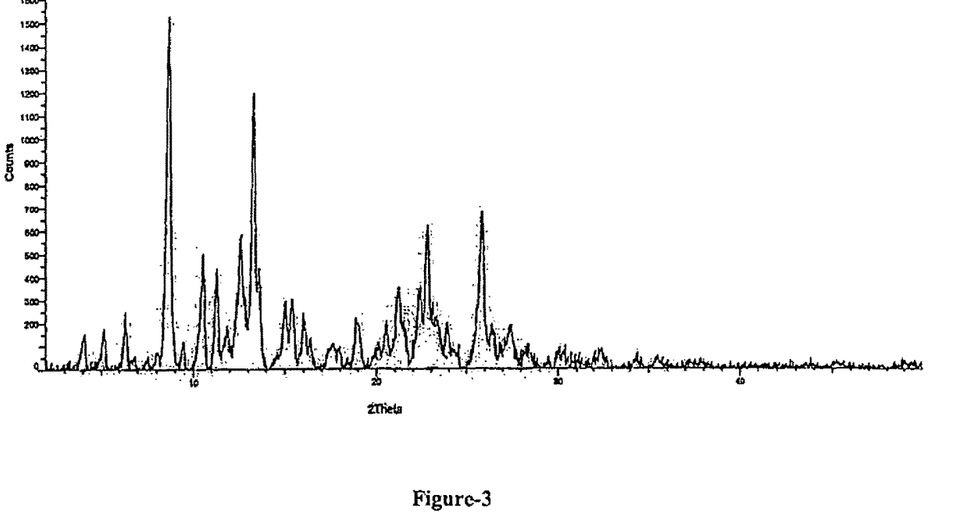
FIG. 3: Illustrates the PXRD pattern of crystalline form-N of N-(4-(6,7-dimethoxy quinolin-4-yloxy)phenyl)-N'-(4-fluorophenyl)cyclopropane-1,1-dicarboxamide hydrochloride salt compound of formula-1b.

The fourth aspect of the present invention provides a crystalline form-N of N-(4-(6,7-dimethoxyquinolin-4-yloxy)phenyl)-N'-(4-fluorophenyl)cyclopropane-1,1-dicarboxamide hydrochloric acid salt compound of formula-1b, characterized by its powder x-ray diffraction pattern having peaks at 4.0, 5.1, 6.3, 7.5, 8.0, 8.6, 9.4, 10.5, 11.2, 11.8, 12.6, 13.3, 13.5, 15.0, 15.3, 16.0, 16.3, 17.5, 17.9, 18.9, 19.9, 20.5, 21.2, 22.3, 22.7, 23.2, 23.8, 25.8, 26.4 and 27.4±0.2 degrees two theta as depicted in figure-3.

In another embodiment of the present invention provides a process for the preparation of crystalline form-N of N-(4-(6,7-dimethoxyquinolin-4-yloxy)phenyl)-N'-(4-fluorophenyl) cyclopropane-1,1-dicarboxamide hydrochloride salt compound of formula-1b, comprising of:
   a) Adding a suitable solvent to N-(4-(6,7-dimethoxyquinolin-4-yloxy)phenyl)-N'-(4-fluorophenyl)cyclopropane-1,1-dicarboxamide hydrochloride salt of compound of formula-1b,
   b) stirring the reaction mixture for 5 hours,
   c) filtering the reaction mixture and drying to get crystalline form-N of N-(4-(6,7-dimethoxyquinolin-4-yloxy)phenyl)-N'-(4-fluorophenyl)cyclopropane-1,1-dicarboxamide hydrochloride salt compound of formula-1b.

Wherein, in step-a) the suitable solvent is selected from chloro solvents, alcohol solvents, ester solvents, nitrile solvents, polar aprotic solvents, hydrocarbon solvents, ether solvents, ketone solvents, polar solvents such as water or mixtures thereof.

The preferred embodiment of the present invention provides a process for the preparation of crystalline form-N of N-(4-(6,7-dimethoxyquinolin-4-yloxy)phenyl)-N'-(4-fluorophenyl)cyclopropane-1,1-dicarboxamide hydrochloride salt compound of formula-1b, comprising of:
   a) Adding isopropanol to N-(4-(6,7-dimethoxyquinolin-4-yloxy)phenyl)-N'-(4-fluoro phenyl)cyclopropane-1,1-dicarboxamide hydrochloride salt of compound of formula-1b,
   b) stirring the reaction mixture 5 hours,
   c) filtering the reaction mixture and drying to get crystalline form-N of N-(4-(6,7-dimethoxyquinolin-4-yloxy)phenyl)-N'-(4-fluorophenyl)cyclopropane-1,1-dicarboxamide hydrochloride salt compound of formula-1b.

Figure 4:
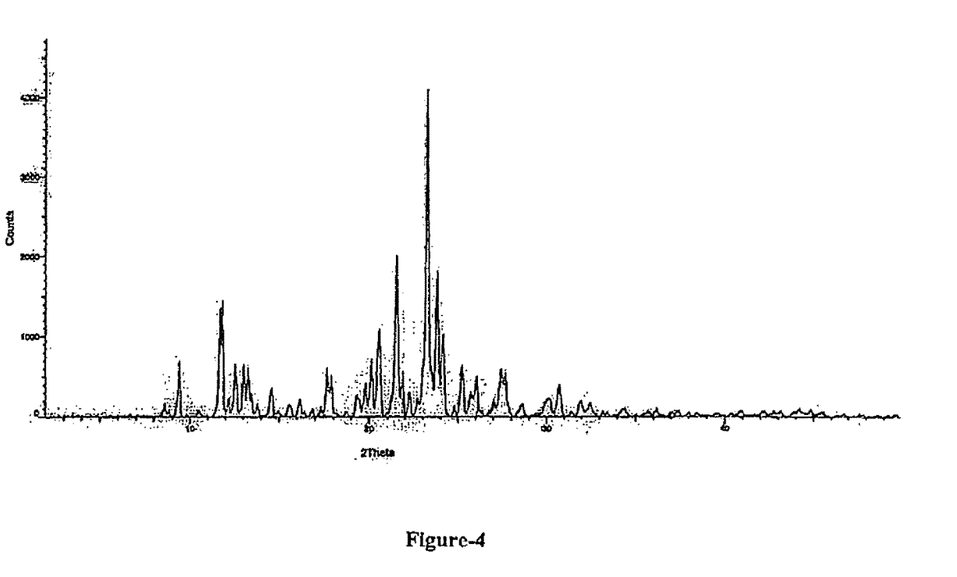
FIG. 4: Illustrates the PXRD pattern of crystalline form-R of N-(4-(6,7-dimethoxy quinolin-4-yloxy)phenyl)-N'-(4-fluorophenyl)cyclopropane-1,1-dicarboxamide hydrochloride salt compound of formula-1b.

The fourth aspect of the present invention provides a crystalline form-R of N-(4-(6,7-dimethoxyquinolin-4-yloxy)phenyl)-N'-(4-fluorophenyl)cyclopropane-1,1-dicarboxamide hydrochloride salt compound of formula-1b, characterized by its powder x-ray diffraction pattern having peaks at 8.5, 9.3, 10.5, 11.6, 11.8, 12.1, 12.5, 12.9, 13.2, 13.7, 14.5, 15.5, 16.1, 16.8, 17.2, 17.6, 17.8, 19.3, 19.7, 20.0, 20.4, 213, 21.8, 22.2, 22.7, 23.2, 23.7, 24.0, 25.2, 25.7, 25.9, 27.0, 27.4, 27.6, 28.5, 30.0, 30.6, 31.9 and 32.3±0.2 degrees two theta as depicted in figure-4.

In another embodiment of the present invention provides a process for the preparation of crystalline form-R of N-(4-(6,7-dimethoxyquinolin-4-yloxy)phenyl)-N'-(4-fluorophenyl) cyclopropane-1,1-dicarboxamide hydrochloride salt compound of formula-1b, comprising of the following steps:
   a) Adding a suitable solvent to N-(4-(6,7-dimethoxyquinolin-4-yloxy)phenyl)-N'-(4-fluorophenyl)cyclopropane-1,1-dicarboxamide compound of formula-1,
   b) adding suitable hydrochloric acid salt to the reaction mixture,
   c) stirring the reaction mixture,
   d) filtering the reaction mixture,
   e) adding a suitable solvent to the compound obtained in step-d),
   f) stirring the reaction mixture,
   g) filtering the reaction mixture and drying to get the crystalline form-R of N-(4-(6,7-dimethoxyquinolin-4-yloxy)phenyl)-N'-(4-fluorophenyl)cyclopropane-1,1-dicarboxamide hydrochloride salt compound of formula-1b.

Wherein, in step-a) and step-e) the suitable solvent is selected from chloro solvents, alcohol solvents, ester solvents, nitrile solvents, polar aprotic solvents, hydrocarbon solvents, ether solvents, ketone solvents, polar solvents such as water or mixtures thereof; in step-b) the suitable hydrochloric acid source is same as defined in step-(c) of the second aspect of the present invention.

The preferred embodiment of the present invention provides a process for the preparation of crystalline form-R of N-(4-(6,7-dimethoxyquinolin-4-yloxy)phenyl)-N'-(4-fluorophenyl)cyclopropane-1,1-dicarboxamide hydrochloride salt compound of formula-1b, comprising of the following steps:
   a) Adding a mixture of tetrahydrofuran and ethyl acetate to N-(4-(6,7-dimethoxy quinolin-4-yloxy)phenyl)-N'-(4-fluorophenyl)cyclopropane-1,1-dicarboxamide compound of formula-1,
   b) adding aqueous hydrochloric acid salt to the reaction mixture,
   c) stirring the reaction mixture,
   d) filtering the reaction mixture,
   e) adding isopropanol to the compound obtained in step-d),
   f) stirring the reaction mixture,
   g) filtering the reaction mixture and drying to get the crystalline form-R of N-(4-(6,7-dimethoxyquinolin-4-yloxy)phenyl)-N'-(4-fluorophenyl)cyclopropane-1,1-dicarboxamide hydrochloride salt compound of formula-1b.

The crude compound of formula-1 was treated with a suitable acid selected from inorganic acids such as hydrochloric acid, hydrobromic acid, sulfuric acid, nitric acid or phosphoric acid; and organic acids such as oxalic acid, maleic acid, malonic acid, tartaric acid, fumaric acid, citric acid, malic acid, succinic acid, mandelic acid, lactic acid, acetic acid, propionic acid, 2-chloromandelate, p-toluene sulfonic acid, ethane-1,2-disulfonic acid, camphor sulfonic acid, ethane sulfonic acid, methane sulfonic acid, naphthalene-2-sulfonic acid, benzene sulfonic acid, adipic acid, glutaric acid, glutamic acid, palmitic acid or aspartic acid to provide its corresponding acid addition salt of compound of formula-1 and further neutralizing the acid addition salt of compound of formula-1 with a suitable base selected from a group consisting of alkali metal carbonates like sodium carbonate, lithium carbonate, potassium carbonate; or an alkali metal hydroxide like sodium hydroxide, potassium hydroxide, lithium hydroxide; or alkali metal bicarbonates like sodium bicarbonate, potassium bicarbonate; or an organic base-like triethylamine, tributylamine, diisopropylethylamine to provide pure compound of formula-1.

Figure 5:
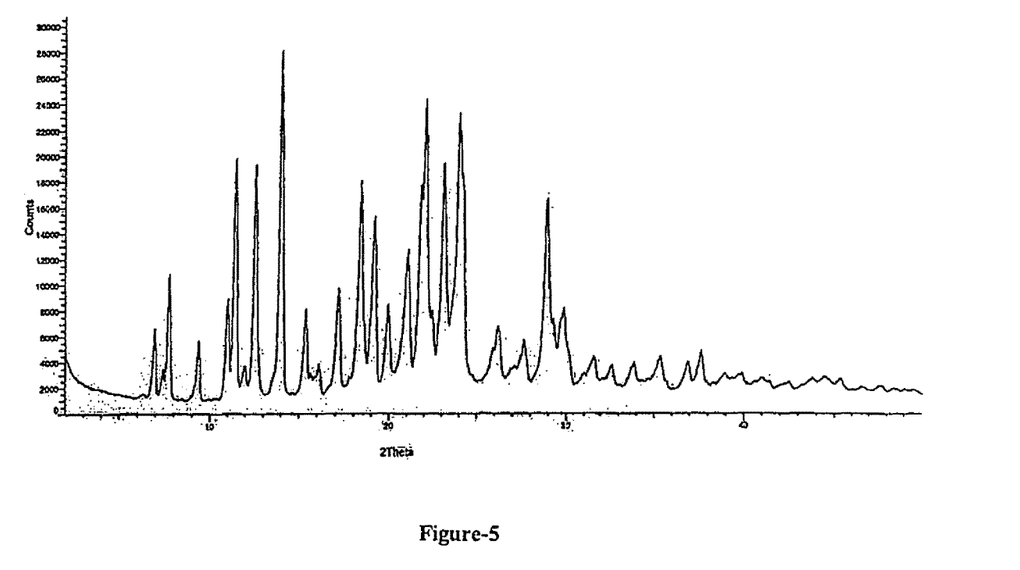

The sixth aspect of the present invention provides novel crystalline form-M of N-(4-(6,7-dimethoxyquinolin-4-yloxy)phenyl)-N'-(4-fluorophenyl)cyclopropane-1,1-dicarboxamide (S)-malate compound of formula-1a, characterized by its powder x-ray diffraction pattern having peaks at 7.0, 7.4, 7.8, 9.4, 11.0, 11.4, 11.9, 12.6, 13.6, 14.0, 15.4, 15.6, 16.1, 17.2, 18.4, 19.2, 19.9, 21.1, 21.8, 22.1, 22.4, 23.1, 24.0, 24.2, 25.8, 26.2, 27.1, 27.6, 28.9, 29.3, 29.9, 30.1, 31.6, 32.5, 33.8, 35.3, 36.8, 37.6 and 39.9±0.2 degrees two theta as depicted in figure-5.

In another embodiment of the present invention provides a process for the preparation of crystalline form-M of N-(4-(6,7-dimethoxyquinolin-4-yloxy)phenyl)-1\l'-(4-fluorophenyl) cyclopropane-1,1-dicarboxamide (S)-malate compound of formula-1a, comprising of the following steps:
   a) Adding a suitable solvent to N-(4-(6,7-dimethoxyquinolin-4-yloxy)phenyl)-N'-(4-fluorophenyl)cyclopropane-1,1-dicarboxamide compound of formula-1,
   b) heating the reaction mixture to a suitable temperature,
   c) adding (L)-malic acid to the reaction mixture,
   d) stirring the reaction mixture, e) cooling the reaction mixture to a suitable temperature and stirring the reaction mixture, f) filtering the precipitated solid and drying to get the crystalline form-M of N-{4-[(6,7-dimethoxyquinolin-4-yloxy]phenyl}-N'-(4-fluorophenyl)cyclopropane-1,1-dicarboxamide (S)-malate compound of formula-1a.

Wherein, in step-a) the suitable solvent is selected from chloro solvents, alcohol solvents, ester solvents, nitrile solvents, polar aprotic solvents, hydrocarbon solvents, ether solvents, ketone solvents, polar solvents such as water or mixtures thereof; in step-b) the suitable temperature is ranging from 30° C. to reflux temperature of the solvent used in the reaction;

in step-e) the suitable temperature is ranging from −50° C. to 0° C.

The preferred embodiment of the present invention provides a process for the preparation of crystalline form-M of N-(4-(6,7-dimethoxyquinolin-4-yloxy)phenyl)-N'-(4-fluorophenyl)cyclopropane-1,1-dicarboxamide (S)-malate compound of formula-1a, comprising of the following steps:
    a) Adding xylene to N-(4-(6,7-dimethoxyquinolin-4-yloxy)phenyl)-N'-(4-fluorophenyl) cyclopropane-1,1-dicarboxamide compound of formula-1,
    b) heating the reaction mixture to 70-75° C.,
    c) adding (L)-malic acid to the reaction mixture,
    d) stirring the reaction mixture,
    e) cooling the reaction mixture to −50° C. and stirring the reaction mixture,
    f) filtering the precipitated solid and drying to get the crystalline form-M of N-(4-(6,7-dimethoxyquinolin-4-yloxy)phenyl)-N'-(4-fluorophenyl)cyclopropane-1,1-dicarboxamide (S)-malate compound of formula-1a.

The another preferred embodiment of the present invention provides a process for the preparation of crystalline form-M of N-(4-(6,7-dimethoxyquinolin-4-yloxy)phenyl)-N'-(4-fluorophenyl)cyclopropane-1,1-dicarboxamide (S)-malate compound of formula-1a, comprising of the following steps:
    a) Adding n-heptane to N-(4-(6,7-dimethoxyquinolin-4-yloxy)phenyl)-N'-(4-fluoro phenyl)cyclopropane-1,1-dicarboxamide compound of formula-1,
    b) heating the reaction mixture to 65-70° C.,
    c) adding (L)-malic acid to the reaction mixture,
    d) stirring the reaction mixture,
    e) cooling the reaction mixture to −50° C. and stirring the reaction mixture,
    f) filtering the precipitated solid and drying to get the crystalline form-M of N-(4-(6,7-dimethoxyquinolin-4-yloxy)phenyl)-N'-(4-fluorophenyl)cyclopropane-1,1-dicarboxamide (S)-malate compound of formula-1a.

The another preferred embodiment of the present invention provides a process for the preparation of crystalline form-M of N-(4-(6,7-dimethoxyquinolin-4-yloxy)phenyl)-N'-(4-fluorophenyl)cyclopropane-1,1-dicarboxamide (S)-malate compound of formula-1a, comprising of the following steps:
    a) Adding methyl tert-butyl ether to N-(4-(6,7-dimethoxyquinolin-4-yloxy)phenyl)-N'-(4-fluorophenyl)cyclopropane-1,1-dicarboxamide compound of formula-1,
    b) heating the reaction mixture to 50-55° C.,
    c) adding (L)-malic acid to the reaction mixture,
    d) stirring the reaction mixture,
    e) cooling the reaction mixture to −50° C. and stirring the reaction mixture,
    f) filtering the precipitated solid and drying to get the crystalline form-M of N-(4-(6,7-dimethoxyquinolin-4-yloxy)phenyl)-N'-(4-fluorophenyl)cyclopropane-1,1-dicarboxamide (S)-malate compound of formula-1a.

The preferred embodiment of the present invention provides a process for the preparation of crystalline form-M of N-(4-(6,7-dimethoxyquinolin-4-yloxy)phenyl)-N'-(4-fluorophenyl)cyclopropane-1,1-dicarboxamide (S)-malate compound of formula-1a, comprising of the following steps:
    a) Adding toluene to N-(4-(6,7-dimethoxyquinolin-4-yloxy)phenyl)-N'-(4-fluorophenyl)cyclopropane-1,1-dicarboxamide compound of formula-1,
    b) heating the reaction mixture to 70-75° C.,
    c) adding (L)-malic acid to the reaction mixture,
    d) stirring the reaction mixture,
    e) cooling the reaction mixture to −50° C. and stirring the reaction mixture,
    f) filtering the precipitated solid and drying to get the crystalline form-M of N-(4-(6,7-dimethoxyquinolin-4-yloxy)phenyl)-N'-(4-fluorophenyl)cyclopropane-1,1-dicarboxamide (S)-malate compound of formula-1a.

N-(4-(6,7-dimethoxyquinolin-4-yloxy)phenyl)-N'-(4-fluorophenyl)cyclopropane-1,1-dicarboxamide (S)-malate compound of formula-1a and hydrochloride salt compound of formula-1b respectively produced according to the present invention are useful in the preparation of pharmaceutical formulation.

The seventh aspect of the present invention provides novel crystalline form-S of N-(4-(6,7-dimethoxyquinolin-4-yloxy)phenyl)-N'-(4-fluorophenyl)cyclopropane-1,1-dicarboxamide (S)-malate compound of formula-1a, Formula-1a characterized by its powder x-ray diffraction pattern having peaks at 6.6, 7.6, 8.2, 10.0, 10.5, 12.5, 13.3, 15.1, 16.4, 18.2, 19.0, 20.2, 20.6, 21.6, 22.6, 25.1, 26.1, 27.0, 28.1, 29.8 and 32.8±0.2 degrees two theta as depicted in figure-1.

In an embodiment of the present invention provides a process for the preparation of crystalline form-S of N-(4-(6,7-dimethoxyquinolin-4-yloxy)phenyl)-N'-(4-fluorophenyl)cyclo Propane-1,1-dicarboxamide (S)-malate compound of formula-1, comprising of;
    a) Adding a suitable solvent to crystalline form-M of N-(4-(6,7-dimethoxyquinolin-4-yl oxy)phenyl)-N'-(4-fluorophenyl)cyclopropane-1,1-dicarboxamide (S)-malate compound of formula-1a,
    b) heating the reaction mixture to a suitable temperature and stirring the reaction mixture,
    c) optionally, filtering the reaction mixture,
    d) adding the obtained filtrate in step-c) to a pre-cooled suitable anti-solvent at suitable temperature,
    e) stirring the reaction mixture,
    f) filtering the precipitated solid and drying to get crystalline form-S of N-(4-(6,7-dimethoxyquinolin-4- yloxy)phenyl)-N'-(4-fluorophenyl)cyclopropane-1,1-di carboxamide (S)-malate compound of formula-1a.

Wherein, in step-b) the suitable temperature is ranging from ambient temperature to the reflux temperature of the solvent used in the reaction;
in step-d) the suitable anti-solvent is selected from chloro solvents and hydrocarbon solvents; the suitable temperature is ranging from −10° C. to 20° C.;
in step-a) and d) the suitable solvent is selected from chloro solvents, alcohol solvents, ester solvents, nitrile solvents, polar aprotic solvents, hydrocarbon solvents, ether solvents, ketone solvents, polar solvents such as water or mixture thereof.

The preferred embodiment of the present invention provides a process for the preparation of crystalline form-S of N-(4-(6,7-dimethoxyquinolin-4-yloxy)phenyl)-N'-(4-fluorophenyl)cyclopropane-1,1-dicarboxamide (S)-malate compound of formula-1a, comprising of;
  a) Adding a mixture of tetrahydrofuran and water to crystalline form-M of N-(4-(6,7-dimethoxyquinolin-4-yloxy)phenyl)-N'-(4-fluorophenyl)cyclopropane-1,1-dicarboxamide (S)-malate compound of formula-1a,
  b) heating the reaction mixture to 60-65° C. and stirring the reaction mixture,
  c) filtering the reaction mixture through hyflow bed,
  d) adding the obtained filtrate in step-c) to a pre-cooled dichloromethane at 0-5° C.,
  e) stirring the reaction mixture,
  f) filtering the precipitated solid and drying to get crystalline form-S of N-(4-(6,7-dimethoxyquinolin-4-yloxy)phenyl)-N'-(4-fluorophenyl)cyclopropane-1,1-di carboxamide (S)-malate compound of formula-1a.

The crystalline form-S of N-(4-(6,7-dimethoxyquinolin-4-yloxy)phenyl)-N'-(4-fluoro phenyl)cyclopropane-1,1-dicarboxamide (S)-malate compound of formula-1a obtained according to the present invention can be prepared by using crystalline form-M of compound of formula-1a disclosed in the present invention or any of the free base compound of formula-1 or compound of formula-1a known in the prior art.

Thermal Stability at 60° C.:
Samples of crystalline form-S of Cabozantinib (S)-malate (3.0 gms) is subjected to heating in a vacuum dryer at 60° C. for 24 hours. The P-XRD pattern was results to show that crystalline form-S of Cabozantinib (S)-malate is stable.

Hygroscopic Stability for 24 Hours:
Samples of crystalline form-S of Cabozantinib (S)-malate (3.0 gms) is kept in the desiccator for 24 hours. The P-XRD pattern was results to show that crystalline form-S of Cabozantinib (S)-malate is stable.

The eighth aspect of the present invention provides a process for the preparation of crystalline form-S of N-(4-(6,7-dimethoxyquinolin-4-yloxy)phenyl)-N'-(4-fluorophenyl)cyclo propane-1,1-dicarboxamide (S)-malate compound of formula-1a, comprising of:
  a) Treating N-(4-(6,7-dimethoxyquinolin-4-yloxy)phenyl)-N'-(4-fluorophenyl)cyclo propane-1,1-dicarboxamide hydrochloride salt with a suitable base in a suitable solvent,
  b) adding a suitable solvent to the reaction mixture and stirring the reaction mixture,
  c) separating both the organic and aqueous layers,
  d) optionally treating the organic layer with carbon,
  e) optionally filtering the organic layer through hyflow bed,
  f) optionally heating the obtained filtrate to a suitable temperature,
  g) adding malic acid to the filtrate,
  h) adding a suitable anti-solvent to the reaction mixture and stirring the reaction mixture,
  i) cooling the reaction mixture to a suitable temperature,
  j) filtering the precipitated solid and dried to provide crystalline form-S of N-(4-(6,7-dimethoxyquinolin-4-yloxy)phenyl)-N'-(4-fluorophenyl)cyclopropane-1,1-dicarboxamide (S)-malate compound of formula-1a.

Wherein, in step-a) the suitable base is selected from organic or inorganic bases; in step-b) the suitable solvent is selected from alcohol solvents, ester solvents, ketone solvents, ether solvents, hydrocarbon solvents, polar aprotic solvents, nitrite solvents, polar solvents like water or mixture thereof; in step-f) the suitable temperature is ranging from 30° C. to reflux temperature of the solvent used; in step-h) the suitable anti-solvent is selected from chloro solvents; in step-i) the suitable temperature is ranging from 20° C. to −20° C.

The preferred embodiment of the present invention provides a process for the preparation of crystalline form-S of N-(4-(6,7-dimethoxyquinolin-4-yloxy)phenyl)-W-(4-fluorophenyl)cyclopropane-1,1-dicarboxamide (S)-malate compound of formula-1a, comprising of:
  a) Treating N-(4-(6,7-dimethoxyquinolin-4-yloxy)phenyl)-N'-(4-fluorophenyl)cyclo propane-1,1-dicarboxamide hydrochloride salt with aqueous sodium carbonate and water,
  b) adding a mixture of ethyl acetate and tetrahydrofuran to the reaction mixture and stirring the reaction mixture,
  c) separating both the organic and aqueous layers,
  d) treating the organic layer with carbon,
  e) filtering the organic layer through hyflow bed,
  f) heating the obtained filtrate to 40-45° C.,
  g) adding malic acid to the filtrate at 40-45° C.,
  h) adding dichloromethane to the reaction mixture and stirring the reaction mixture at 40-45° C.,
  i) cooling the reaction mixture to 0-5° C.,
  j) filtering the precipitated solid and dried to provide crystalline form-S of N-(4-(6,7-dimethoxyquinolin-4-yloxy)phenyl)-N'-(4-fluorophenyl)cyclopropane-1,1-dicarboxamide (S)-malate compound of formula-1a.

The preferred embodiment of the present invention provides a process for the preparation of crystalline forth-S of N-(4-(6,7-dimethoxyquinolin-4-yloxy)phenyl)-N'-(4-fluorophenyl)cyclopropane-1,1-dicarboxamide (S)-malate compound of formula-1a, comprising of:
  a) Treating N-(4-(6,7-dimethoxyquinolin-4-yloxy)phenyl)-N'-(4-fluorophenyl)cyclo propane-1,1-dicarboxamide hydrochloride salt with aqueous sodium carbonate and water,
  b) adding a mixture of ethyl acetate and tetrahydrofuran to the reaction mixture and stirring the reaction mixture,
  c) separating both the organic and aqueous layers,
  d) treating the organic layer with carbon,
  e) filtering the organic layer through hyflow bed,
  f) heating the obtained filtrate to 40-45° C.,
  g) adding dichloromethane to the reaction mixture and stirring the reaction mixture at 40-45° C.,
  h) adding malic acid to the filtrate at 40-45° C.,
  i) cooling the reaction mixture to 0-5° C.,
  j) filtering the precipitated solid and dried to provide crystalline form-S of N-(4-(6,7-dimethoxyquinolin-4-yloxy)phenyl)-N'-(4-fluorophenyl)cyclopropane-1,1-dicarboxamide (S)-malate compound of formula-1a.

The preferred embodiment of the present invention provides a process for the preparation of crystalline form-S of N-(4-(6,7-dimethoxyquinolin-4-yloxy)phenyl)-N'-(4-fluorophenyl)cyclopropane-1,1-dicarboxamide (S)-malate compound of formula-1a, comprising of:

a) Treating N-(4-(6,7-dimethoxyquinolin-4-yloxy)phenyl)-N'-(4-fluorophenyl)cyclo propane-1,1-dicarboxamide hydrochloride salt with aqueous sodium carbonate and water,
b) adding a mixture of ethyl acetate and tetrahydrofuran to the reaction mixture and stirring the reaction mixture,
c) separating both the organic and aqueous layers,
d) treating the organic layer with carbon,
e) filtering the organic layer through hyflow bed,
f) adding a mixture of ethyl acetate, tetrahydrofuran and malic acid to the filtrate,
g) adding dichloromethane to the reaction mixture and stirring the reaction mixture,
h) cooling the reaction mixture to 0-5° C.,
i) filtering the precipitated solid and dried to provide crystalline form-S of N-(4-(6,7-dimethoxyquinolin-4-yloxy)phenyl)-N'-(4-fluorophenyl)cyclopropane-1,1-dicarboxamide (S)-malate compound of formula-1a.

In another embodiment of the present invention provides a process for the preparation of crystalline form-S of N-(4-(6,7-dimethoxyquinolin-4-yloxy)phenyl)-N'-(4-fluorophenyl) cyclopropane-1,1-dicarboxamide (S)-malate compound of formula-1a, comprising of:

a) Treating N-(4-(6,7-dimethoxyquinolin-4-yloxy)phenyl)-N'-(4-fluorophenyl)cyclo propane-1,1-dicarboxamide hydrochloride salt with a suitable base in a suitable solvent,
b) adding a suitable solvent to the reaction mixture and stirring the reaction mixture,
c) separating both the organic and aqueous layers,
d) optionally treating the organic layer with carbon,
e) optionally filtering the organic layer through hyflow bed,
f) optionally heating the obtained filtrate to a suitable temperature,
g) adding malic acid to the filtrate,
h) adding the reaction mixture obtained in step-g) to a pre-cooled solvent and stirring the reaction mixture,
i) filtering the precipitated solid and dried to provide crystalline form-S of N-(4-(6,7-dimethoxyquinolin-4-yloxy)phenyl)-N'-(4-fluorophenyl)cyclopropane-1,1-dicarboxamide (S)-malate compound of formula-1a.

Wherein, in step-a) the suitable base is selected from organic or inorganic bases; in step-b) the suitable solvent is selected from alcohol solvents, ester solvents, ketone solvents, ether solvents, hydrocarbon solvents, polar aprotic solvents, nitrile solvents, polar solvents like water or mixture thereof; in step-h) the suitable solvent is selected from chloro solvents.

The preferred embodiment of the present invention provides a process for the preparation of crystalline form-S of N-(4-(6,7-dimethoxyquinolin-4-yloxy)phenyl)-N'-(4-fluorophenyl)cyclopropane-1,1-dicarboxamide (S)-malate compound of formula-1a, comprising of:

a) Treating N-(4-(6,7-dimethoxyquinolin-4-yloxy)phenyl)-N'-(4-fluorophenyl)cyclopropane-1,1-dicarboxamide hydrochloride salt with aqueous sodium carbonate in water,
b) adding a mixture of ethyl acetate and tetrahydrofuran to the reaction mixture and stirring the reaction mixture,
c) separating both the organic and aqueous layers,
d) treating the organic layer with carbon,
e) filtering the organic layer through hyflow bed,
f) adding malic acid to the filtrate,
g) adding the reaction mixture obtained in step-f) to a pre-cooled dichloromethane and stirring the reaction mixture at 0-5° C.,
h) filtering the precipitated solid and dried to provide crystalline form-S of N-(4-(6,7-dimethoxyquinolin-4-yloxy)phenyl)-N'-(4-fluorophenyl)cyclopropane-1,1-dicarboxamide (S)-malate compound of formula-1a.

The crystalline form-S of N-(4-(6,7-dimethoxyquinolin-4-yloxy)phenyl)-N'-(4-fluoro phenyl)cyclopropane-1,1-dicarboxamide (S)-malate compound of formula-1a according to the present invention is having purity greater than 99.95% by HPLC.

The starting materials compound of formula-2 and compound of formula-4 used in the present invention can be prepared by any of the prior known process.

Crystalline form-S of N-(4-(6,7-dimethoxyquinolin-4-yloxy)phenyl)-N'-(4-fluoro phenyl)cyclopropane-1,1-dicarboxamide (S)-malate compound of formula-1a obtained according to the present invention is having particle size distribution $D_{90}$<100 μm.

N-(4-(6,7-dimethoxyquinolin-4-yloxy)phenyl)-N'-(4-fluorophenyl)cyclopropane-1,1-dicarboxamide compound of formula-1a and formula-1b produced by the present invention can be further micronized or milled in a conventional techniques to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

The invention also encompasses pharmaceutical compositions comprising compound of formula-1 or salts thereof of the present invention. As used herein, the term "pharmaceutical compositions" or "pharmaceutical formulations" include tablets, pills, powders, liquids, suspensions, emulsions, granules, capsules, suppositories, or injection preparations.

The N-(4-(6,7-dimethoxyquinolin-4-yloxy)phenyl)-N'-(4-fluorophenyl)cyclopropane-1,1-dicarboxamide (S)-malate compound of formula-1a obtained according to the present invention is having purity greater than 99.9% by HPLC.

P-XRD Method of Analysis:

PXRD analysis of compounds produced by the present invention were carried out using BRUKER IDS ADVANCE/AXS X-Ray diffractometer using Cu Kα radiation of wavelength 1.5406 A° and continuous scan speed of 0.03°/min.

PSD Method of Analysis:

Particle size distribution (PSD) analysis was performed using Malvern Mastersizer 2000 instrument.

The process of the present invention can be represented schematically as follows:

Formula-1a
Cabozantinib (S)-Malate

The process described in the present invention was demonstrated in examples illustrated below. These examples are provided as illustration only and therefore should not be construed as limitation of the scope of the invention.

EXAMPLES

Example-1

Preparation of Crystalline Form-M of Cabozantinib Hydrochloride Salt (Formula-1b Thionyl chloride (180.4 gms) was slowly added to the mixture of 1-((4-fluorophenyl) carbamoyl)cyclopropane carboxylic acid (112.9 gms) and tetrahydrofuran (600 ml) at 25-30° C. and stirred for 5 hours at the same temperature. The reaction mixture was slowly added to a pre-cooled mixture of 4-((6,7-dimethoxyquinolin-4-yloxy)aniline (100 gms), aqueous potassium carbonate solution (418.5 gms of potassium carbonate in 600 ml of water) and tetrahydrofuran (600 ml) at 0-5° C. Raised the temperature of the reaction mixture to 25-30° C. and stirred for 2 hours at the same temperature. Both the organic and aqueous layers were separated. Extracted the aqueous layer with ethyl acetate. Combined the organic layers. Aqueous hydrochloric acid solution (75 ml of HCl in 725 ml of water) was added to the organic layer at 25-30° C. and stirred the reaction mixture for 3 hours at the same temperature. Filtered the precipitated solid, washed with tetrahydrofuran and ethyl acetate, To the obtained compound, isopropanol (22.0 lts) was added at 25-30° C. and stirred for 3 hours at the same temperature. Filtered the solid, washed with isopropanol and dried to get the title compound.
Yield: 152 gms; Chloride content: 7.0%.
The P-XRD pattern of the obtained compound was depicted in figure-1.

Example-2: Preparation of Crystalline Form-S of Cabozantinib Hydrochloride Salt (Formula-1b Dimethyl sulfoxide (700 ml) was added to the obtained compound in example-1 at 25-30° C. and stirred for 45 minutes at the same temperature. Filtered the reaction mixture. Ethyl acetate (2.1 lts) was added to the obtained filtrate at 25-30° C. and stirred for 3 hours at the same temperature. Filtered the precipitated solid, washed with ethyl acetate and dried to get the title compound.

Yield: 169.3 gms; M.R: 185-190° C.; Chloride content: 7.3%; Purity by HPLC: 99.83%.

The P-XRD pattern of the obtained compound was depicted in figure-2.

Example-3: Preparation of Cabozantinib (S)-Malate (Formula-1a

A mixture of water (840 ml) and N-(4-((6,7-dimethoxyquinolin-4-yloxy)phenyl)-N-(4-fluorophenyl) cyclopropane-1,1-dicarboxamide hydrochloride (120 gms) was stirred for 10 minutes at 25-30° C. Aqueous sodium carbonate solution was added to the reaction mixture at 25-30° C. and stirred for 10 minutes at the same temperature. Tetrahydrofuran (900 ml) and ethyl acetate (900 ml) were added to the reaction mixture at 25-30° C. and stirred for 10 minutes at the same temperature. Both the organic and aqueous layers were separated and aqueous layer was extracted twice With tetrahydrofuran and ethyl acetate mixture. Combined the organic layers and washed with aqueous sodium chloride solution. Carbon powder was added to the organic layer at 25-30° C. and stirred for 15 minutes at the same temperature. Filtered the reaction mixture through hyflow bed and washed with tetrahydrofuran. Distilled off the solvent completely from the obtained filtrate under reduced pressure and co-distilled with tetrahydrofuran. To the obtained compound, tetrahydrofuran (1300 ml) and water (14 ml) were added at 25-30° C. Heated the reaction mixture to 60-65° C. and stirred for 15 minutes at the same temperature. The reaction mixture was slowly added to a solution of L-malic acid (34.5 gms) and methyl isobutyl ketone (3.0 lts) and seeding crystals of compound of formula-1a at 25-30° C. and stirred the reaction mixture for 3 hours at the same temperature. Filtered the reaction mixture and washed with methyl isobutyl ketone. To the obtained compound, methyl isobutylketone was added at 25-30° C. and stirred for 3 hours at the same temperature. Filtered the reaction mixture, washed with methyl isobutylketone and dried to get the title compound.

Yield: 113.2 gms; M.R: 182-187° C.; Purity by HPLC: 99.98%; M-Acid impurity: Not detected; Acid impurity: Not detected; Hydroxy impurity: Not detected; Desfluoro impurity: 0.04%; 2-fluoro impurity: Not detected; 3-fluoro impurity: Not detected; N-oxide impurity: Not detected and HIUI: 0.05%.

Before micronization: Particle size distribution: $D_{90}$: 47.97 µm; $D_{50}$: 8.82 µm; $D_{10}$: 3.26 µm.

After micronization: Particle size distribution: $D_{90}$: 15.5 µm; $D_{50}$: 7.4 µm; $D_{10}$: 2.8 µm.

Example-4: Preparation of Crystalline Form-N of Cabozantinib Hydrochloride Salt (Formula-1b Aqueous hydrochloric acid solution was added to N-{4-[(6,7-dimethoxyquinolin-4-yl oxy]phenyl}-N'-(4-fluorophenyl)cyclopropane-1,1-dicarboxamide compound of formula-1 (163 gm) at 25-30° C. and stirred for 3 hours at the same temperature. Filtered the precipitated solid, washed with tetrahydrofuran and ethyl acetate, To the obtained compound, isopropanol (2.2 lts) was added at 25-30° C. and stirred for 5 hours at the same temperature. Filtered the solid, washed with isopropanol and dried to get the title compound.

Yield: 152 gms; Chloride content: 6.4%.

The P-XRD pattern of the obtained compound was depicted in figure-3.

Example-5: Preparation of Crystalline Form-R of Cabozantinib Hydrochloride Salt (Formula-1b Tetrahydrofuran (1080 ml) and ethyl acetate (720 ml) were added to N-{4-[(6,7-dimethoxyquinolin-4-yloxy]phenyl}-N'-(4-fluorophenyl)cyclopropane-1,1-dicarboxamide (150 gms) at 25-30° C. Aqueous hydrochloric acid (67.5 ml of hydrochloric acid in 900 ml of water) was added to the reaction mixture at 25-30° C. and stirred for 3 hours at the same temperature. Filtered the reaction mixture and washed with a mixture of ethyl acetate and tetrahydrofuran. Washed the obtained compound with water and isopropanol. To the obtained compound, isopropanol (2.0 lts) was added at 25-30° C. and stirred for 3 hours at the same temperature. Filtered the solid, washed with isopropanol and dried to get the title compound.

Yield: 149.02 gms; M.R: 240-245° C.; Chloride content: 6.3%; Purity by HPLC: 99.80%.

The P-XRD pattern of the obtained compound was depicted in figure-4.

Example-6: Preparation of Crystalline Form-M of Cabozantinib (S)-Malate

A mixture of toluene (50 ml) and N-{4-[(6,7-dimethoxyquinolin-4-yloxy]phenyl}-N'-(4-fluorophenyl)cyclopropane-1,1-dicarboxamide (5 gms) was stirred for 10 minutes at 25-30° C. Heated the reaction mixture to 70-75° C. L-malic acid (1.6 gms) was added to the reaction mixture at 70-75° C. and stirred for 60 minutes at the same temperature. Cooled the reaction mixture to −50° C. and stirred for 60 minutes at the same temperature. Filtered the precipitated solid and dried to get the title compound. Yield: 4.0 gms; Malate content: 23.6%. The P-XRD pattern of the obtained compound was depicted in figure-5.

Example-7: Preparation of Crystalline Form-M of Cabozantinib (S)-Malate

A mixture of xylene (50 ml) and N-{4-[(6,7-dimethoxyquinolin-4-yloxy]phenyl}-N'-(4-fluorophenyl) cyclopropane-1,1-dicarboxamide (5 gms) was stirred for 10 minutes at 25-30° C. Heated the reaction mixture to 70-75° C. L-malic acid (1.6 gms) was added to the reaction mixture at 70-75° C. and stirred for 60 minutes at the same temperature. Cooled the reaction mixture to −50° C. and stirred for 60 minutes at the same temperature. Filtered the precipitated solid and dried to get the title compound. Yield: 4.5 gms; Malate content: 22.8%. The P-XRD pattern of the obtained compound was depicted in figure-5.

Example-8: Preparation of Crystalline Form-M of Cabozantinib (S)-Malate

A mixture of n-heptane (20 ml) and N-{4-[(6,7-dimethoxyquinolin-4-yloxy]phenyl}-N'-(4-fluorophenyl) cyclopropane-1,1-dicarboxamide (2 gms) was stirred for 10 minutes at 25-30° C. Heated the reaction mixture to 70-75° C. L-malic acid (0.64 gms) was added to the reaction mixture at 70-75° C. and stirred for 60 minutes at the same temperature. Cooled the reaction mixture to −50° C. and stirred for 60 minutes at the same temperature. Filtered the precipitated solid and dried to get the title compound. Yield: 1.2 gms; Malate content: 22.8%.

The P-XRD pattern of the obtained compound was depicted in figure-5.

Example-9: Preparation of Crystalline Form-M of Cabozantinib (S)-Malate

A mixture of methyl tert-butyl ether (20 ml) and N-{4-[(6,7-dimethoxyquinolin-47 yloxy]phenyl}-M-(4-fluorophenyl) cyclopropane-1,1-dicarboxamide (2 gms) was stirred for 10 minutes at 25-30° C. Heated the reaction mixture to 50-55° C. L-malic acid (0.64 gms) was added to the reaction mixture at 50-55° C. and stirred for 60 minutes at the same temperature. Cooled the reaction mixture to −50° C. and stirred for 60 minutes at the same temperature. Filtered the precipitated solid and dried to get the title compound.
Yield: 1.2 gms; Malate content: 23.1%.
The P-XRD pattern of the obtained compound was depicted in figure-S.

Example-10: Preparation of Crystalline Form-M of Cabozantinib (S)-Malate

A mixture of xylene (250 ml) and N-{4-[(6,7-dimethoxy-quinolin-4-yloxy]phenyl}-N'-(4-fluorophenyl) cyclopropane-1,1-dicarboxamide (25 gms) was stirred for 10 minutes at 25-30° C. Heated the reaction mixture to 70-75° C. L-malic acid (8.5 gms) was added to the reaction mixture at 70-75° C. and stirred for 60 minutes at the same temperature. Cooled the reaction mixture to −50° C. and stirred for 60 minutes at the same temperature. Filtered the precipitated solid and dried to get the title compound.
Yield: 24.0 gms.
The P-XRD pattern of the obtained compound was depicted in figure-5.

Example-11: Preparation of Crystalline Form-S of Cabozantinib (S)-Malate

Figure 6:
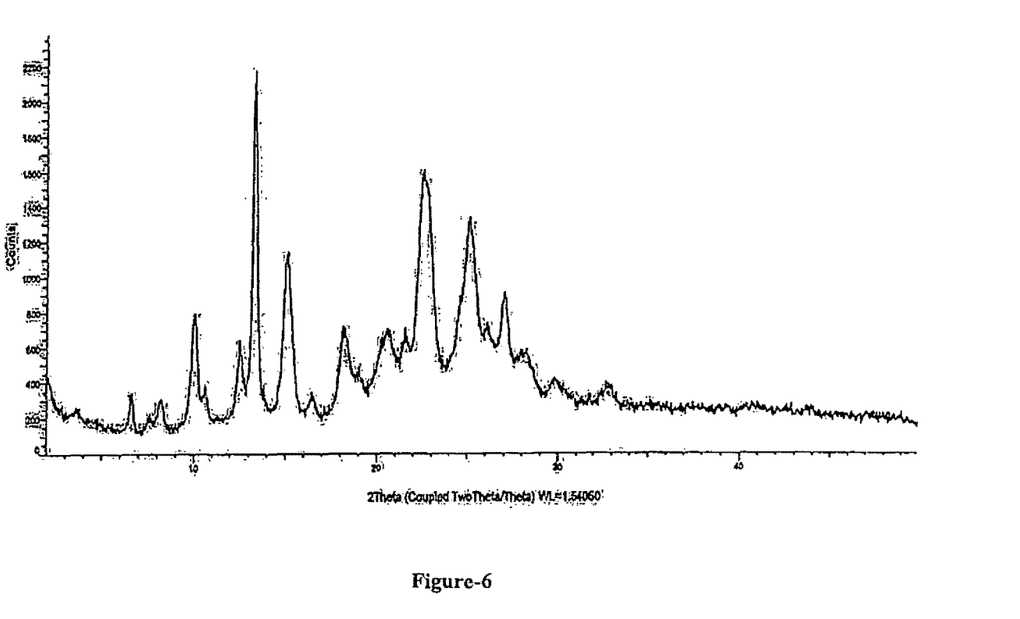

Tetrahydrofuran (500 ml) and water (50 ml) were added to N-(4-(6,7-dimethoxy quinolin-4-yloxy)phenyl)-N'-(4-fluorophenyl)cyclopropane-1,1-dicarboxamide (S)-malate (50 gms) at 25-30° C. and stirred for 10 minutes at the same temperature. Heated the reaction mixture to 60° C. and stirred for 15 minutes at the same temperature. The obtained clear solution was slowly added to pre-cooled dichloromethane (1000 ml) at 0-5° C. and stirred for 60 minutes at the same temperature. Filtered the precipitated solid and dried to get the title compound. Yield: 43.0 gms.
Water content: 2.4%; L-malic acid content: 20.6%; Purity by HPLC: 99.97%;
The P-XRD pattern of the obtained compound is depicted in figure-6.
Particle size distribution: $D_{90}$: 29.02 μm; $D_{50}$: 9.99 μm.

Example-12: Preparation of Crystalline Form-S of Cabozantinib (S)-Malate

Tetrahydrofuran (500 ml) and water (50 ml) were added to crystalline form-M of N-(4-(6,7-dimethoxyquinolin-4-yloxy)phenyl)-N'-(4-fluorophenyl)cyclopropane-1,1-dicarboxamide (S)-malate (50 gms) at 25-30° C. and stirred for 10 minutes at the same temperature. Heated the reaction mixture to 60° C. and stirred for 15 minutes at the same temperature. Filtered the reaction mixture to through hyflow bed. The obtained particle free clear solution was slowly added to pre-cooled dichloromethane (1000 ml) at 0-5° C. and stirred for 60 minutes at the same temperature. Filtered the precipitated solid and dried to get the title compound. Yield: 39.9 gms.
The P-XRD pattern of the obtained compound is depicted in figure-6.

Example-13: Preparation of Crystalline Form-S of Cabozantinib (S)-Malate

Aqueous sodium carbonate solution was added to a mixture of N-(4-(6,7-dimethoxy quinolin-4-yloxy)phenyl)-N'-(4-fluorophenyl)cyclopropane-1,1-dicarboxamide hydrochloride (10 gms) and water (70 ml) at 25-30° C. and stirred for 10 minutes at the same temperature. Ethyl acetate (75 ml) and tetrahydrofuran (75 ml) were added to the reaction mixture at 25-30° C. and stirred for 10 minutes at the same temperature. Both the organic and aqueous layers were separated and aqueous layer was extracted with a mixture of tetrahydrofuran and ethyl acetate. Combined the organic layers and washed with aqueous sodium chloride solution. Carbon powder (1 gm) was added to organic layer at 25-30° C. and stirred for 10 minutes at the same temperature. Filtered the reaction mixture through hyflow bed and washed with tetrahydrofuran. Heated the obtained filtrate to 40-45° C. Malic acid (2.8 gms) was slowly added to the obtained filtrate at 40-45° C. Dichloromethane was slowly added to the reaction mixture at 40-45° C. and stirred for 10 minutes at the same temperature. Cooled the reaction mixture to 0-5° C. and stirred for 3 hours at the same temperature. Filtered the precipitated solid and dried to get the title compound.
Yield: 8.0 gms.
The P-XRD pattern of the obtained compound is depicted in figure-6.

Example-14: Preparation of Crystalline Form-S of Cabozantinib (S)-Malate

Aqueous sodium carbonate solution was added to a mixture of N-(4-(6,7-dimethoxy quinolin-4-yloxy)phenyl)-N'-(4-fluorophenyl)cyclopropane-1,1-dicarboxamide hydrochloride (10 gms) and water (70 ml) at 25-30° C. and stirred for 10 minutes at the same temperature. Ethyl acetate (75 ml) and tetrahydrofuran (75 ml) were added to the reaction mixture at 25-30° C. and stirred for 10 minutes at the same temperature. Both the organic and aqueous layers Were separated and aqueous layer was extracted with a mixture of tetrahydrofuran and ethyl acetate. Combined the organic layers and washed with aqueous sodium chloride solution. Carbon powder (1 gm) was added to organic layer at 25-30° C. and stirred for 10 minutes at the same temperature. Filtered the reaction mixture through hyflow bed and washed with tetrahydrofuran. Heated the obtained filtrate to 40-45° C. Dichloromethane (100 ml) was added to the obtained filtrate at 40-45° C. Malic acid (2.8 gms) was added to the reaction mixture at 50-55° C. and stirred for 10 minutes at the same temperature. Cooled the reaction mixture to 0-5° C. and stirred for 3 hours at the same temperature. Filtered the precipitated solid and dried to get the title compound.
Yield: 7.8 gms.
The P-XRD pattern of the obtained compound is depicted in figure-6.

Example-15: Preparation of Crystalline Form-S of Cabozantinib (S)-Malate

Aqueous sodium carbonate solution was added to a' mixture of N-(4-(6,7-dimethoxy quinolin-4-yloxy)phenyl)-

N'-(4-fluorophenyl)cyclopropane-1,1-dicarboxamide hydrochloride (50 gms) and water (350 ml) at 25-30° C. and stirred for 10 minutes at the same temperature. Ethyl acetate (375 ml) and tetrahydrofuran (375 ml) were added to the reaction mixture at 25-30° C. and stirred for 10 minutes at the same temperature. Both the organic and aqueous layers were separated and aqueous layer was extracted with a mixture of tetrahydrofuran and ethyl acetate. Combined the organic layers and washed with aqueous sodium chloride solution. Carbon powder (4.0 gms) was added to organic layer at 25-30° C. and stirred for 10 minutes at the same temperature. Filtered the reaction mixture through hyflow bed and washed with tetrahydrofuran. Malic acid (14.4 gms) was added to the obtained filtrate at 25-30° C. The reaction mixture was slowly added to a pre-cooled dichloromethane at 0-5° C. and stirred for 1½ hour at the same temperature. Filtered the precipitated solid, washed with dichloromethane and dried to get the title compound.
Yield: 41.0 gms.
The P-XRD pattern of the obtained compound is depicted in figure-6.

Example-16: Preparation of Crystalline Form-S of Cabozantinib (S)-Malate

Aqueous sodium carbonate solution was added to a mixture of N-(4-(6,7-dimethoxy quinolin-4-yloxy)phenyl)-N'-(4-fluorophenyl)cyclopropane-1,1-dicarboxamide hydrochloride (50 gms) and water (350 ml) at 25-30° C. and stirred for 10 minutes at the same temperature: Ethyl acetate (375 ml) and tetrahydrofuran (375 ml) were added to the reaction mixture at 25-30° C. and stirred for 10 minutes at the same temperature. Both the organic and aqueous layers were separated and aqueous layer was extracted with a mixture of tetrahydrofuran and ethyl acetate. Combined the organic layers and washed with aqueous sodium chloride solution. Carbon powder (4.0 gms) was added to organic layer at 25-30° C. and stirred for 10 minutes at the same temperature. Filtered the reaction mixture through hyflow bed and washed with tetrahydrofuran. Malic acid was dissolved in a mixture of ethyl acetate and tetrahydrofuran and this solution was added to the obtained filtrate at 25-30° C. Dichloromethane was added to the reaction mixture at 25-30° C. Cooled the reaction mixture to 0-5° C. and stirred for 60 minutes at the same temperature: Filtered the precipitated solid, washed with dichloromethane and dried to get the title compound.
Yield: 43.0 gms.
The P-XRD pattern of the obtained compound is depicted in figure-6.

Example-17: Preparation of Cabozantinib Hydrochloride Salt (Formula-1b

Thionyl chloride (36.10 kgs) was slowly added to the mixture of 1-((4-fluorophenyl) carbamoyl)cyclopropane carboxylic acid (22.60 kgs) and tetrahydrofuran (120 lts) at 25-30° C. and stirred for 9 hours at the same temperature. The reaction mixture was slowly added to a pre-cooled mixture of 4-((6,7-dimethoxyquinolin-4-yloxy)aniline (20.0 kgs), aqueous potassium carbonate solution (83.70 kgs of potassium carbonate in 120 lts of water) and tetrahydrofuran (120 lts) at 0-5° C. Raised the temperature of the reaction mixture to 25-30° C. and stirred for 2 hours at the same temperature. Both the organic and aqueous layers were separated and water was added to the aqueous layer at 25-30° C. Extracted the aqueous layer with ethyl acetate. Combine the organic layers. Aqueous hydrochloric acid solution (15 lts of HCl in 145 lts of water) was, added to the organic layer at 25-30° C. and stirred the reaction mixture for 3 hours at the same temperature. Filtered the precipitated solid, washed with tetrahydrofuran and ethyl acetate. To the obtained compound, water (lot-4) was added at 25-30° C. and stirred for 2 hours at the same temperature. Filtered the reaction mixture and washed with water. To the obtained compound, water (595 lts) and hydrochloric acid (1.0 lts) were added at 25-30° C. and stirred for 2 hours at the same temperature. Filtered the reaction mixture and washed with water. To the obtained compound, isopropanol (435 lts) was added at 25-30° C. and stirred for 3 hours at the same temperature. Filtered the solid, washed with isopropanol and dried to get the title compound. Dimethyl sulfoxide (235 lts) was added to the obtained compound at 25-30° C. and stirred for 45 minutes at the same temperature. Filtered the reaction mixture. Ethyl acetate (720 lts) was added to the obtained filtrate at 25-30° C. and stirred for 3 hours at the same temperature. Filtered the precipitated solid, washed with ethyl acetate and dried to get the title compound.
Yield: 32.99 kgs; Purity by HPLC: 99.85%.

Example-18: Preparation of Cabozantinib (S)-Malate (Formula-1a

A mixture of water (135 lts) and N-(4-((6,7-dimethoxyquinolin-4-yloxy)phenyl)-N-(4-fluorophenyl)cyclopropane-1,1-dicarboxamide hydrochloride (20.0 kgs) was stirred for 10 minutes at 25-30° C. Aqueous sodium carbonate solution was added to the reaction mixture at 25-30° C. and stirred for 10 minutes at the same temperature. Tetrahydrofuran (150 lts) and ethyl acetate (15 lts) were added to the reaction mixture at 25-30° C. and stirred for 10 minutes at the same temperature. Both the organic and aqueous layers were separated and aqueous layer was extracted twice with tetrahydrofuran and ethyl acetate mixture. Combined the organic layers and washed with aqueous sodium chloride solution. Carbon powder was added to the organic layer at 25-30° C. and stirred for 15 minutes at the same temperature. Filtered the reaction mixture through hyflow bed and washed with tetrahydrofuran. Distilled off the solvent completely from the obtained filtrate under reduced pressure and co-distilled with tetrahydrofuran. To the obtained, compound, tetrahydrofuran (216 lts) and water (2.2 lts) were added at 25-30° C. Heated the reaction mixture to 60-65° C. and stirred for 20 minutes at the same temperature. The reaction mixture was slowly added to a solution of L-malic acid (5.70 kgs) and methyl isobutyl ketone (500 lts) and seeding crystals of compound of formula-1a at 25-30° C. and stirred the reaction mixture for 3 hours at the same temperature. Filtered the reaction mixture and washed with methyl isobutyl ketone. To the obtained compound, methyl isobutylketone (40 lts) was added at 25-30° C. and stirred for 3 hours at the same temperature. Filtered the reaction mixture, washed with methyl isobutylketone and dried to get the title compound. The obtained compound was micronized using conventional techniques to get the desired particle size. Methyl isobutyl ketone (200 lts) was added to the micronized compound at 25-30° C. and stirred form 3 hours at the same temperature. Filtered the compound and washed with methyl isobutyl ketone and dried to get title compound.
Yield: 21.34 kgs; Purity by HPLC: 99.96%.

We claim:
1. A crystalline form-S of N-(4-(6,7-dimethoxyquinolin-4-yloxy)phenyl)-N'-(4-fluorophenyl)cyclopropane-1,1-dicarboxamide (S)-malate compound of formula-1a,

Formula-1a characterized by its powder x-ray diffraction pattern having peaks at 10.0±0.2 and further comprising peaks at 8.2 and 13.3±0.2 degrees two theta.

2. A crystalline form-S of N-(4-(6,7-dimethoxyquinolin-4-yloxy)phenyl)-N'-(4-fluorophenyl)cyclopropane-1,1-dicarboxamide (S)-malate compound of formula-1a according to claim 1 characterized by its powder x-ray diffraction having peaks at 10.0±0.2 and further comprising peaks at 15.1 and 18.2±0.2 degrees two theta.

3. A crystalline form-S of N-(4-(6,7-dimethoxyquinolin-4-yloxy)phenyl)-N'-(4-fluorophenyl)cyclopropane-1,1-dicarboxamide (S)-malate compound of formula-1a according to claim 1 further characterized by its powder x-ray diffraction pattern having peaks at 6.6, 7.6, 10.5, 12.5, 16.4, 19.0, 20.2, 20.6, 21.6, 22.6, 25.1, 26.1, 27.0, 28.1, 29.8 and 32.8±0.2 degrees two theta.

4. A crystalline form-S of N-(4-(6,7-dimethoxyquinolin-4-yloxy)phenyl)-N'-(4-fluorophenyl)cyclopropane-1,1-dicarboxamide (S)-malate compound of formula-1a according to claim 1 further characterized by its powder x-ray diffraction pattern as depicted in figure-6.

5. A process for the preparation of crystalline form-S of compound of formula-1a according to claim 1, comprising
a) stirring a mixture of compound of formula-1a in a solvent or a mixture of solvents,
b) filtering the solid and drying to the solid to obtain crystalline form-S of compound of formula-1a.

6. A process for the preparation of crystalline form-S of compound of formula-1a according to claim 5, comprising:
a) adding a solvent to a compound of formula-1a,
b) heating the mixture to a suitable temperature,
c) adding the obtained solution to an anti-solvent,
d) filtering the precipitated solid and drying to obtain crystalline form-S of compound of formula-1a,
wherein the solvent used in step-a) is selected from alcohol solvents, ester solvents, nitrile solvents, polar aprotic solvents, hydrocarbon solvents, ether solvents, ketone solvents, polar solvents such as water or mixture thereof;
the suitable temperature in step-b) is ranging from ambient temperature to the reflux temperature of the solvent used in the reaction;
the anti-solvent used in step-c) is chloro solvents.

7. The process according to claim 6, comprising:
a) adding a mixture of tetrahydrofuran and water to a compound of formula-1a,
b) heating the mixture,
c) adding the obtained solution to dichloromethane, and
d) filtering the precipitated solid and drying to obtain crystalline form-S of compound of formula-1a.

8. A process for the preparation of crystalline form-S of compound of formula-1a according to claim 1, comprising:

a) treating compound of formula-1b with a base in a solvent,
b) adding a solvent to the mixture,
c) adding malic acid to the solution,
d) adding an anti-solvent to the mixture, and
e) filtering the precipitated solid and dried to provide crystalline form-S of compound of formula-1a,
wherein, the base used in step-a) is selected from organic base or inorganic base;
the solvent used in step-b) is selected from alcohol solvents, ester solvents, ketone solvents, ether solvents, hydrocarbon solvents, polar aprotic solvents, nitrile solvents, polar solvents like water or mixture thereof;
the anti-solvent used in step-d) is chloro solvents.

9. The process according to claim 8, comprising:
a) treating compound of formula-1b with aqueous sodium carbonate and water,
b) adding a mixture of ethyl acetate and tetrahydrofuran to the mixture,
c) adding malic acid to the solution,
d) adding dichloromethane to the mixture, and
e) filtering the precipitated solid and dried to provide crystalline form-S of compound of formula-1a.

10. A process for the preparation of crystalline form-S of compound of formula-1a according to claim 1, comprising:
a) treating compound of formula-1b with aqueous sodium carbonate and water,
b) adding a mixture of ethyl acetate and tetrahydrofuran to the mixture
c) adding dichloromethane to the mixture,
d) adding malic acid to the solution, and
e) filtering the precipitated solid and dried to provide crystalline form-S of compound of formula-1a.

11. A process for the preparation of crystalline form-S of compound of formula-1a according to claim 1, comprising:
a) treating compound of formula-1b with aqueous sodium carbonate and water,
b) adding a mixture of ethyl acetate, tetrahydrofuran and malic acid to the solution,
c) adding dichloromethane to the mixture, and
d) filtering the precipitated solid and dried to provide crystalline form-S of compound of formula-1a.

12. A process for the preparation of crystalline form-S of compound of formula-1a according to claim 1, comprising:
a) treating compound of formula-1b with a base in a solvent,
b) adding a solvent to the mixture,
c) adding malic acid to the solution,
d) adding the mixture to a solvent, and
e) filtering the precipitated solid and dried to provide crystalline form-S of compound of formula-1a.

13. The process according to claim 12, wherein the base used in step-a) is selected from organic base or inorganic base; the solvent used in step-b) is selected from the group consisting of alcohol solvents, ester solvents, ketone solvents, ether solvents, hydrocarbon solvents, polar aprotic solvents, nitrile solvents, polar solvents like water and a mixture thereof; and the solvent used in step-d) is chloro solvents.

14. A process for the preparation of crystalline form-S of compound of formula-1a according to claim 1, comprising:
a) treating compound of formula-1b with aqueous sodium carbonate in water,
b) adding a mixture of ethyl acetate and tetrahydrofuran to the mixture,
c) adding malic acid to the solution, d) adding the mixture to dichloromethane, and
e) filtering the precipitated solid and dried to provide crystalline form-S of compound of formula-1a.

15. A pharmaceutical composition comprising crystalline form-S of compound of formula-1a and a pharmaceutical acceptable carrier or diluent according to claim 1.

* * * * *